United States Patent [19]

Wood

[11] Patent Number: 5,290,707
[45] Date of Patent: Mar. 1, 1994

[54] METHOD FOR DETECTION OF MICROORGANISMS

[75] Inventor: Sheila J. Wood, Edgewood, Md.

[73] Assignee: The United States of America as represented by the Secretary of the Army, Washington, D.C.

[21] Appl. No.: 797,754

[22] Filed: Nov. 25, 1991

[51] Int. Cl.$^5$ ............... G01N 33/544; G01N 33/545; G01N 33/546

[52] U.S. Cl. .................... 436/523; 435/7.93; 435/973; 436/533; 436/534; 436/536; 436/538; 436/541; 436/800; 436/824

[58] Field of Search ........... 436/523, 533, 534, 536, 436/538, 541, 800, 824; 435/973, 7.93

[56] References Cited

U.S. PATENT DOCUMENTS

| | | | |
|---|---|---|---|
| 4,184,849 | 1/1980 | Cambiaso et al. | 436/523 |
| 4,305,925 | 12/1981 | Kapmeyer et al. | 436/523 |
| 4,665,020 | 5/1987 | Saunders | 436/523 |
| 5,071,774 | 12/1991 | Vorpahl et al. | 436/800 |

FOREIGN PATENT DOCUMENTS

| | | | |
|---|---|---|---|
| 332373 | 6/1983 | None | 435/973 |
| 0263731 | 4/1988 | European Pat. Off. | 436/523 |
| 2627286 | 8/1989 | France | 435/973 |
| 0095357 | 4/1988 | Japan | 435/973 |
| 0158354 | 6/1989 | Japan | 435/973 |

*Primary Examiner*—David Saunders
*Assistant Examiner*—Christopher L. Chin
*Attorney, Agent, or Firm*—Anthony T. Lane; Edward Goldberg; Werten F. Bellamy

[57] ABSTRACT

A microorganism detection system provides initial warning, confirmation of identity, and recognition of pathogenic factors in microorganisms from environmental samples. The method and apparatus of the invention uses different sized antibody coated microspheres which react with unknown antigens, are sized by electronic volume sizing, and are sorted by size. The sized particles are quantitated in addition to being sized. The microsphere sizes indicate the presence of specific microorganism groups.

The samples can be further analyzed using fluorescent microspheres which agglutinate with the sized microspheres. The presence of specific microorganisms is indicated by a change in the fluorescence of the sample.

5 Claims, 3 Drawing Sheets

FIG. 3A
FIG. 3C
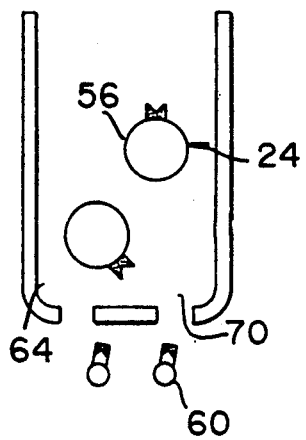
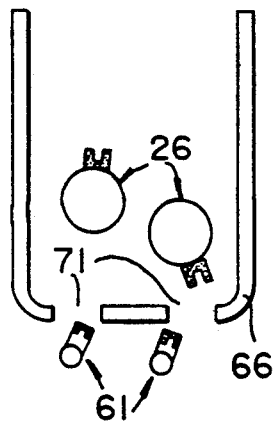
FIG. 3B
FIG. 4
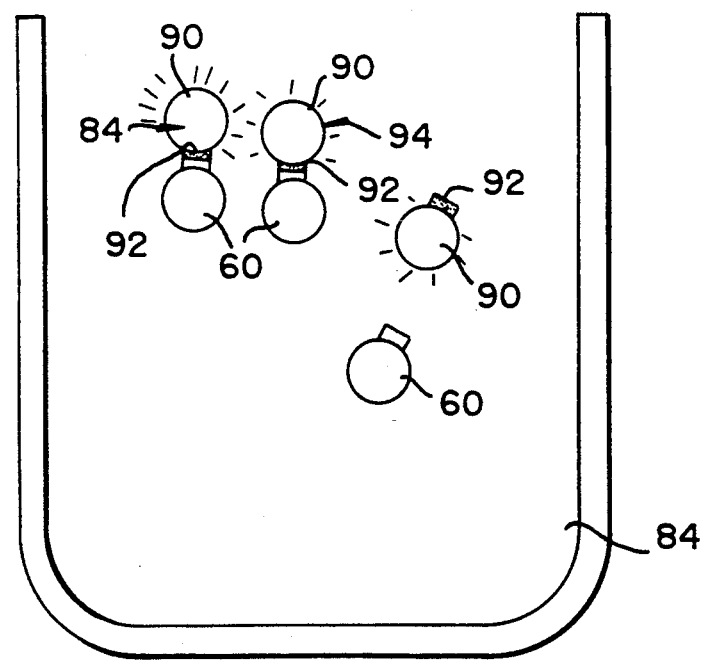

METHOD FOR DETECTION OF MICROORGANISMS

BACKGROUND OF THE INVENTION

1. Field of the Invention

The present invention relates to microorganism detection and sorting systems.

2. Prior Art

Most methods for the analysis of bacteria are based on the availability of a significant amount of biomass taken directly from plated growth media. Some direct methods, such as antigen-antibody agglutination reactions and deoxyribonucleic acid (DNA) hybridization reactions, target organisms in clinical specimens without growing them on plated media. Likewise, these methods require 1,000 to 10,000 organisms for positive reactions. The requirement for significant amounts of material in order to get a reaction, makes direct screening from environmental samples difficult due to the low concentrations of organisms. Recognition of 10-100 bacteria from an environmental sample requires ultra-critical sensitivity. This sensitivity must be built into a system in two ways, viz., in the signal generated from organism capture and in the instrumentation used to read that signal. Several such methods have been tried, and some have been successful, but these methods involve time-consuming preparative and analytical steps in large, sophisticated, laboratory-supported equipment.

A primary goal of this field device for microorganism detection, is to have recognition capability for 10 to 100 genetically engineered organisms per milliliter in environmental samples. Present identification methods are inadequate for three reasons: a large amount of biomass is required to identify organisms; the presence of more than one species cannot be determined without prior growth and isolation which takes 24-48 hours; and the characterization of genetically engineered organisms by biochemical profiles is meaningless, as these profiles can change with genetic manipulation. Thus, composite microorganism components such as DNA must be targeted, instead of the ability of the microorganism to ferment carbohydrates or use proteins.

Factors best targeted in genetically engineered microorganisms include those factors which endow them with special disease causing potential. Some examples include, the ability to colonize mammalian cells via specific attachment factors, the carriage of genes coding for the presence of pathogenic determinants, and cell wall components which play a part in pathogenesis of disease, produced by highly conserved regions of the DNA. Target approaches for these factors differ considerably from conventional identification schemes and, understandably, the methods for recognition of these factors must differ, especially since the targeted pathogenic factors are likely to be present in very small quantities.

The first signal should provide an indication of threat to rule in (or out) microorganisms found in one of four major classifications. This separation can be accomplished by filtration, cell sizing, or immunologic signal recognition. Groups to be separated include selected amoebae, selected yeasts, gram-negative and gram-positive bacteria, and single or double stranded RNA or DNA viruses.

SUMMARY OF THE INVENTION

It is an object of the present invention to separate organisms by size determination and to confirm the microorganism classification.

It is a further object to characterize the pathogenic potential of microorganisms.

It is a further object of the invention to provide a warning system for microorganisms that can provide a preliminary warning within three minutes of sample acquisition.

It is a further object of the invention to provide a microorganism warning system for microorganisms that can be precalibrated with a calibration storage option for immediate readiness in field situations.

It is a further object of the invention to provide a microorganism warning system that is easy to operate.

It is a further object of the invention to provide a microorganism warning system that requires low maintenance and has easy part replacement.

It is a further object of the invention to provide a microorganism warning system that is compact and usable in the field.

It is a further object of the invention to provide a microorganism warning system that uses standard electrical sources.

It is a further object of the invention to provide a microorganism warning system that is able to count and size particles 0.4 to 1200 microns in diameter.

It is a further object of the invention to provide a microorganism warning system that is able to confirm the presence of pathogens and further specifies their pathogenic potential.

These and other objects of the invention are achieved using a method and apparatus for detecting microorganisms.

In one embodiment, the present invention comprises a method for detecting antigens comprising:

providing screening bodies comprising an antibody attached to a first size microsphere;

providing agglutinating bodies comprising a second size microsphere which is relatively large in size as compared with a said first size microsphere and an antigen which is attached to said relatively large microsphere and which can agglutinate with an antibody on one of the screening bodies;

mixing at least one type of unknown antigen with the agglutinating bodies to form a fluid mixture;

mixing the screening bodies with the fluid mixture to allow the at least one type of unknown antigen to attach to a first screening body to form an antigen-antibody-microsphere complex if the at least one unknown antigen agglutinates with a first antibody on the first screening body and to allow a first agglutinating body to agglutinate with the first screening body to form an agglutinating body-antigen-antibody-microsphere complex if the at least one type of unknown antigen does not agglutinate with the first antibody; and passing the fluid mixture through a filtering means which separates the antigen-antibody-microsphere complex from the agglutinating body-antigen-antibody-microsphere complex and the agglutinating bodies.

In a second embodiment, the invention comprises an apparatus for detecting antigens comprising:

screening bodies for reacting with at least one type of unknown antigen present in a sample to be tested, each of the screening bodies comprising an antibody attached to a small microsphere;

agglutinating bodies for agglutinating with the antibodies on the screening bodies when the at least one type of unknown antigen is not present in the sample, each of the agglutinating bodies comprising a known antigen which agglutinates with the antibody on at least one of the screening bodies and a large microsphere to which the known antigen is attached;

a first mixing zone wherein the at least one type of unknown antigen is mixed with the agglutinating bodies to form a fluid mixture;

a second mixing zone wherein the screening bodies are mixed with the fluid mixture to allow the at least one type of unknown antigen to attach to the screening bodies to form antigen-antibody-microsphere complexes if the at least one type of unknown antigen agglutinates with a receptive antibody on the screening bodies and to allow each of the agglutinating bodies to agglutinate with a free antibody on the screening bodies to form agglutinating-body-antigen-antibody-microsphere complexes when no unknown antigen agglutinates with the free antibody; and a filtering means for separating the antigen-antibody-microsphere complexes from the agglutinating-body-antigen-antibody-microsphere complexes and the agglutinating bodies.

BRIEF DESCRIPTION OF THE DRAWINGS

FIGS. 3A-3C are a schematic cross-sectional view to an enlayed scale of the filters of the apparatus of FIG. 1.

FIG. 4 is a schematic cross-sectional view to enlayed scale of one of the collection vessels of the apparatus of FIG. 1.

DETAILED DESCRIPTION OF THE INVENTION

Figure 1:
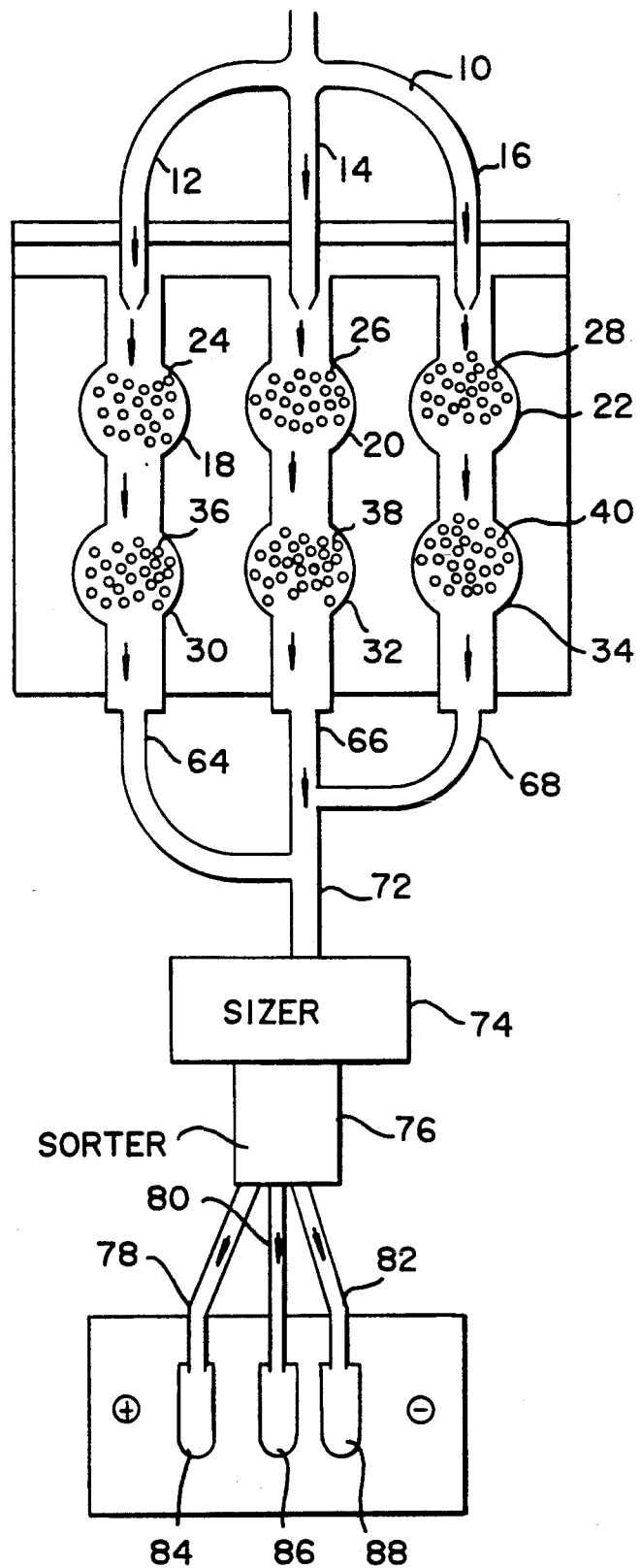
FIG. 1 is a schematic cross-sectional view, partially in block diagram form, of an apparatus for microorganism detection in accordance with a preferred embodiment of the invention.

Among other advantages thereof, the invention is designed for use in the field, uses reagents that are stable for at least 12-months, requires no special provisions for electricity, and has low maintenance requirements. The method and apparatus of the invention are sensitive enough to detect low numbers of organisms and provide a warning within three minutes of sample introduction into the system.

The preferred apparatus for practicing the method of the invention uses Coulter volume sizing as an early three minute warning for major groups of organisms, 0.04 to 50 microns in diameter. A suitable electronic volume sizing device can be precalibrated for immediate readiness, requires no labile reagents, has low maintenance requirements, provides cell counts and size distributions within 30 to 90 seconds, and can detect size differences as minute as 0.05 cubic microns.

In electronic particle sizing a dilute suspension of particles in an electrolyte solution is stirred and drawn through a small aperture by a vacuum source. Current passing through the aperture between two electrodes enables the particles to be sensed by momentary changes in electrical impedance as they pass through the aperture. Each particle displaces its volume of electrolyte within the aperture itself. These changes in impedance are detected and presented as a series of voltage pulses. The height of each pulse is essentially proportional to the volume of the particle that produces it.

Several thousand particles per second may be individually counted and sized using this technique. Counting is performed when the particle suspension is drawn through the aperture, the quantity of which is precisely controlled by a mercury nanometer. Electrical contacts in the mercury column allow the system to count and size particles in an exact, reproducible volume.

In the system of the invention, a preferred particle sizer is the Coulter ® Multisizer which can size particles from 0.4 microns to 1200 microns in diameter. The number of cells present, the volume of particles, and the surface area of particles can also be measured quickly and easily. Results are displayed as number of particles, or may be converted by mathematical weighting to area or volume of particles. A window anywhere within the full range of observation can be chosen to achieve high resolution analysis, up to one part in 25,600. The use of Coulter electronics for evaluation of bacteria and yeasts has been well documented.

Electronically, the particle sizer can be constructed to allow for charge deflection sorting after particle size determination. A viewing window can also be inserted between the size sensor and a charge deflector if increased sensitivity is needed. Sorting gathers organisms for confirmatory and pathogenic factor recognition.

Specific targeting of pathogenic factors by antigen-antibody, adhesion-receptor, and DNA hybridization reactions can be accomplished using fluorescent tags. Fluorescence detection can easily be implemented as an extended portion of this initial warning instrument. Fluorescence recognition has stability advantages (up to 12 months for most compounds) and can detect low numbers of organisms. Mercury arc lamps, which require no special electrical provisions, can also be used as well as laser detection.

A preferred embodiment of the invention is described below with reference to the drawing figures. The initial three minute warning, confirmation of the presence of pathogens, and the definitive pathogenic factor assays are combined in the system of the invention. In the description, the term "antigen" includes the microorganism which contains a particular antigen.

As shown in FIG. 1, a sample containing one or more unknown antigens is collected and fed as a fluid stream through a channel 10 which in turn splits into three flow channels 12, 14 and 16. After entering each flow channel 12, 14 or 16, the fluid stream enters first mixing zones 18, 20 and 22, respectively, which contain agglutinating bodies 24, 26 and 28, respectively in depressions in the walls of thereof. In the first mixing zones 18, 20 and 22, the antigens in the fluid stream are mixed with agglutinating bodies 24, 26 and 28 to form fluid mixtures. These fluid mixtures continue to travel along channels 12, 14 and 16 until they reach second mixing zones 30, 32, and 34, respectively, which contain screening bodies 36, 38 and 40, respectively, in depressions in the walls thereof.

The agglutinating bodies 24, 26, and 28 in first mixing zones 18, 20 and 22 can be the same or different, and the agglutinating bodies in each of the first mixing zones may be a mixture of different types of agglutinating bodies. Similarly, the screening bodies 36, 38 and 40 in the second mixing zones can be the same or different, and the screening bodies in each second mixing zone may be a mixture of different types of screening bodies.

Figure 2C:
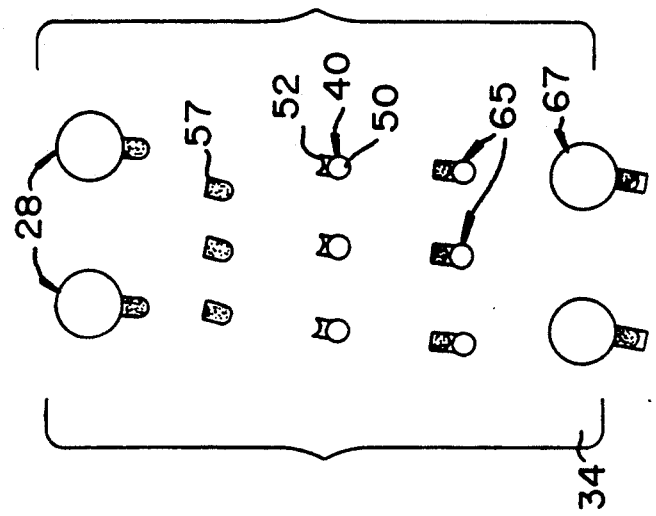
FIGS. 2A-2C are a schematic cross-sectional view of the second mixing regions of the apparatus of FIG. 1 showing the agglutinating bodies, antigens and screening bodies of the invention in diagrammatic form.
Figure 2B:
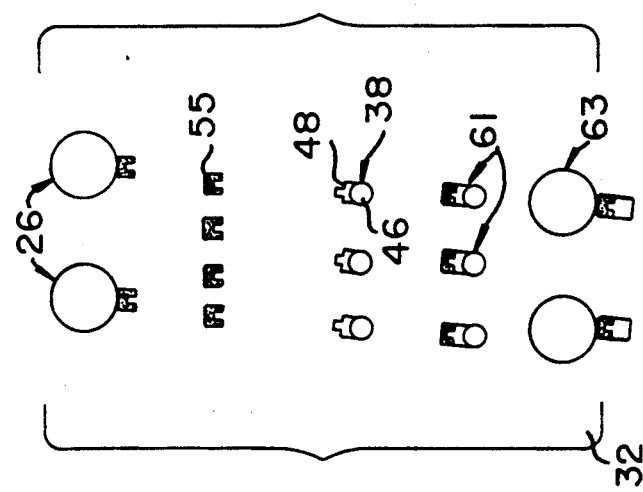
Figure 2A:
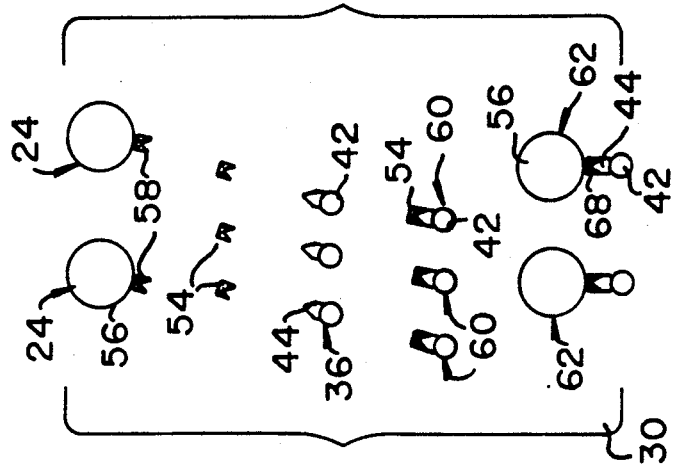

As shown in diagrammatic form in FIG. 2, for the purposes of illustration, the screening bodies 36 of mixing zone 30 FIG. 1 each comprise an 0.8 μm microsphere 42 to which there is attached an antibody 44 for an RNA virus, screening bodies 38 of mixing zone 34 of FIG. 1 each comprise a 1.6 μm microsphere 46 to which there is attached an antibody 48 for a gram positive bacteria and screening body 40 is a 2.4 μm microsphere 50 to which there is attached an antibody 52 for yeasts. In the mixing zone 30, a fluid mixture which contains agglutinating bodies 24 of FIG. 1 and unknown antigens indicated at 54 comes in contact with the screening bodies 36 while in zones 32 and 34 the unknown antigens are denoted 55 and 57, respectively.

As is also shown in FIG. 2, for mixing zone 30, the agglutinating bodies 24 of FIG. 1 each comprise of a 1.5 to 4 μm microsphere 56 to which there is attached an antigen 58 which competes with antigen 54 for the binding site on antibody 44. If an unknown antigen 54 is present, it will agglutinate or bind with antibody 44 to form antigen-antibody-microsphere complex 60. However, if the unknown antigen 54 is not present in the fluid stream, antigen 58 will react at the binding site on antibody 44 and an agglutinating body-antigen-antibody-microsphere complex 62.

Similar reactions occur in the mixing zone 32 wherein the antigen-antibody-microsphere complex is denoted 61 and the agglutinating body-antigen-antibody-microsphere on flux is denoted 63 and in zone 34 wherein the antigen-antibody-microsphere complex is denoted 65 and the agglutinating body antigen-antibody-microsphere complex is denoted 67. While only one competing antigen 58 is shown in zone 30 in FIG. 2, additional antigens 58 may be attached to microspheres 56 so that number of agglutinating bodies 56 necessary for binding up screening bodies 36 is reduced.

Referring again to FIG. 1, respective filters 64, 66 and 68 are disposed downstream of regions 30, 32 and 33. FIG. 3 illustrates schematically what occurs at filters 64, 66 and 68. Referring first to filter 64, it is assumed that an antigen 54 is present in the sample being tested, and thus, an antigen-antibody-microsphere complex 60 is formed which is of a size passes through pores 70 provided in filter 64. The size of microspheres 56 of agglutinating bodies 24 is chosen so that they will not pass through the pores 70 in filter 64. A similar situation is illustrated with respect to filter 66. Wherein antigen 54 is present is the sample, and the antigen-antibody-microsphere complexes 61 pass through pores 71. However, if a particular antigen is not present in the sample, as illustrated in connection with filter 68 where antigen 57 is not present, only agglutinating body-antigen-antibody-microsphere complexes 67 will form and these are too large relative to pores 73 in filter 68 and thus are unable to pass through filter 68.

Referring again to FIG. 1, microspheres that pass through filters 64, 66 and 68 are recombined in a channel 72 for passage through a volume sizer 74 which measures the quantity and size of particles present. A preferred volume sizer is the Coulter® Multisizer. Because the different antibodies are placed on selected sizes of microspheres, the size measurements also indicate how many antigens have been agglutinated by each antibody. This simplifies instrument requirements considerably. Size determinations are sufficient at this stage of recognition, but fluorescence properties can be used in later determinations.

As shown in FIG. 1, after sizing, the microsphere complexes flow into a sorter 76 where they are sorted by charge pulse deflection. A suitable method for charge pulse deflection is described in Shapiro H. M., ed. *Practical Flow Cytometry.* New York: Alan A. Liss, Inc., (1988); 107, the entire disclosure of which is hereby incorporated by reference. While sizing is often done in a closed environment, a viewing window can be added for greater sensitivity. A sorting apparatus that includes such a viewing window is described in Melamed MR, ed. *Flow Cytometry and Cell Sorting,* New York: Wiley and Sons (1979); 633, the entire disclosure of which is hereby incorporated by reference. The information obtained from the sizer and sorter gives quantity and major classification of organisms present. After the microsphere complexes are sorted, they pass through tubes 78, 80 and 82 and are collected in collection vessels 84, 86 and 88 for further analysis.

In each of collection vessels 84, 86, and 88 the microsphere complexes are exposed to fluorescent microspheres to which there are attached antibodies which agglutinate with the complexes. For the sake of convenience, the reactions which occur of only one of the collection vessels 84 will be discussed in detail below. However, it should be understood that similar reactions occur between the complexes and fluorescent microspheres in each of collection vessels 84, 86 and 88.

FIG. 4 illustrates what occurs in collection vessel 84. Collection vessel 84 contains fluorescent microspheres 90 having attached thereto specific monoclonal antibodies 92 to pathogenic factors (antigens). The fluorescent microspheres 90 each contain a fluorescent marker which absorbs energy in the area that a complex 60 containing the pathogenic factor being tested would emit energy. If the emission wavelength of the complexes 60 is read using a conventional fluorescence detection device (not shown), then a decrease in the fluorescence signal of the complexes 60 indicates that fluorescent microspheres 90 have agglutinated with complexes 60 to form fluorescent complexes 94. If no decrease in the signal is measured, then the pathogenic factor being tested is not present in the sample. The agglutination of microspheres can be measured using light scattered detection or optical density reads.

The complex 60 is preferably excited to emit a fluorescence signal using a mercury arc lamp or a laser beam. When a laser beam is used, it is preferably small and should not require special electrical considerations.

Using microspheres as carriers provides the apparatus of the invention several advantages over conventional antigen detection apparatus. First, instrumentation for sizing can be made simple when dealing with predetermined sphere sizes. Second, viral particles and spores are too small to be picked up by Coulter volume sensing unless attached to a larger sphere. Third, labelling the antigen or antibody directly with fluorescent molecules reduces the original fluorescence by as much as 50%. Fourth, having the fluorescent dyes in the microspheres allows for more material per molecule, thus more sensitive determinations. Fifth, predetermining the different sizes of spheres eliminates any overlap in size that may occur when dealing with the microorganisms alone, for example, bacteria can be in the same size range as basidiospores of Cryptococcus. Sixth, the fluorescent carrier serves as an indication of instrument function from the beginning of flow to the end, as they are standard calibration tools for these instruments. Sensitivities of $10^{-14}$ mol/L for enzymatic antigen-antibody reactions have been obtained using microspheres as carriers in flow cytometry as described in Saunders et al., "Amplified flow-cytometric separation-free fluorescence immunoassays." *Clin. Chem.* (1985), 31:2020-2023 and Sharpless et al., "Flow cytofluorimetry: discrimination between single cells and cell aggregates by direct size measurements" *Acta Cytologia* (1985), 19:577-581.

While the device of the present invention has been discussed with the use of three possible antigens to be detected, it should be clear that more than three types of antigens can be tested by altering the device and increasing the number of sizes of microspheres used to provide for the possibility of sorting and detecting more than three types of antigens.

In a preferred embodiment, six different major groups of organisms are sorted and identified using the apparatus and method of the invention: amoebae, yeasts, gram positive bacteria, gram negative bacteria, RNA viruses and DNA viruses.

The larger amoebae, 10-30 microns in diameter, Entamoeba, Naeqleria, Giardia, and Acanthamoeba can be captured with a polyclonal antibody prepared against a preparation of cell wall material from all four genera or against a lectin common to all.

Yeasts can be detected using a polyclonal antibody directed against sterols found in their cell walls. The major groups of interest include Cryptococcus, Blastomyces, Histoplasma, and Coccidioides (arthrospores). They are definitively identified using monoclonals prepared against pathogenic serotypes of the particular species of interest.

Bacteria are designated first as gram-positive, by polyclonal recognition of teichoic acid cell wall fraction, or as gram-negative, by polyclonal antibody recognition of lipopolysaccharide (LPS), a gram-negative cell wall component. Further identification of specific pathogenic factors is based on DNA hybridization.

Viruses are separated by anti-uracil antibody (RNA) and anti-thymidine (DNA). Acridine orange staining is performed for determination of single or double strandedness. Further identification may involve genetic amplification and hybridization assays.

Rhodamine dyes which excite and emit in the 530-610 nm range are preferably used as fluorescent markers for the fluorescent microspheres. These wavelengths avoid interferences from substances normally found in the environment which fluoresce in the 400-500 nm range.

The microorganism detection apparatus of the invention is able to count and size particles (antigens) 0.4 to 1200 microns in diameter.

I claim:

1. A method for detecting one or more unknown antigens comprising the steps of:
   a. providing multiple screening bodies, each comprising an antibody specific for each of said unknown antigens attached to a different size microsphere,
   b. providing multiple agglutinating bodies each comprising an antigen, which can bind with an antibody on one of said screening bodies attached to a second size microsphere which is larger than the microspheres of said screening bodies;
   c. mixing at least one type of unknown antigen with said agglutinating bodies to form multiple fluid mixtures;
   d. mixing each of said screening bodies with the fluid mixtures of step c to form multiple second fluid mixtures wherein in each second fluid mixtures (i) each unknown antigen binds to an antibody on one of said screening bodies to form an unknown antigen-antibody-microsphere complex when said unknown antigen is present, or (ii) said agglutinating bodies bind with said screening bodies to form an agglutinating body-antigen-antibody-microsphere complex when said unknown antigen is not present
   e. filtering said second fluid mixtures through a filter having a pore size that prevents the agglutinating bodies from passing through the filter resulting in the separation of any agglutinating body antigen-antibody-microsphere complexes present therein from said second fluid mixtures;
   f. passing the filtered second fluid mixtures which contain the unknown antigen-antibody-microsphere complexes through a volume sizer to measure the quantity and particle size of the microsphere complexes, and continuing the flow of the unknown antigen-antibody-microsphere complexes into a sorter which sorts and routes the unknown antigen-antibody-microsphere complexes by the size of each screening body to separate vessels each containing a second antibody bound to fluorescent microspheres, wherein each of said second antibodies is specific for one of the unknown antigens in each of the vessels;
   g. exposing any unknown antigen-antibody-microsphere complexes to the fluorescent microspheres contained in said vessels, wherein said second antibodies on said fluorescent microspheres specifically bind with the unknown antigen-antibody-microsphere complexes; and
   h. measuring a fluorescent signal from said fluorescent microspheres in each of the vessels to determine the presence of each of the unknown antigens.

2. The method of claim 1, wherein said large microspheres are about 1.5 μm-40 μm in diameter and said small microspheres are about 0.5 to 3.0 μm in diameter.

3. The method of claim 1, wherein said fluorescent microspheres contain rhodamine dyes which emit in the 530 to 610 nm range.

4. The method of claim 1, wherein fluorescent microsphere-unknown antigen-antibody microsphere complexes are measured using light scatter detection.

5. The method of claim 1, wherein fluorescent microsphere-unknown antigen-antibody microsphere complexes are measured using optical density read.

* * * * *